United States Patent
Chopra et al.

(10) Patent No.: US 6,589,174 B1
(45) Date of Patent: Jul. 8, 2003

(54) TECHNIQUE AND APPARATUS FOR ULTRASOUND THERAPY

(75) Inventors: Rajiv Chopra, Etobicoke (CA); Michael J. Bronskill, Toronto (CA)

(73) Assignee: Sunnybrook & Women's College Health Sciences Centre, Toronto (CA)

(*) Notice: Subject to any disclaimer, the term of this patent is extended or adjusted under 35 U.S.C. 154(b) by 251 days.

(21) Appl. No.: 09/692,448

(22) Filed: Oct. 20, 2000

(51) Int. Cl.[7] .................................................. A61B 8/12
(52) U.S. Cl. ........................ 600/439; 600/411; 600/459; 601/2
(58) Field of Search ................................. 600/459, 439, 600/411; 601/2

(56) References Cited

U.S. PATENT DOCUMENTS

| | | | |
|---|---|---|---|
| 4,276,491 A | * 6/1981 | Daniel | 310/317 |
| 4,756,808 A | 7/1988 | Utsumi et al. | |
| 4,870,972 A | 10/1989 | Maerfeld et al. | |
| 4,963,782 A | 10/1990 | Bui et al. | |
| 5,230,334 A | * 7/1993 | Klopotek | 601/3 |
| 5,295,484 A | 3/1994 | Marcus et al. | 128/660 |
| 5,400,788 A | * 3/1995 | Dias et al. | 600/459 |
| 5,460,595 A | 10/1995 | Hall et al. | 601/2 |
| 5,524,624 A | * 6/1996 | Tepper et al. | 600/439 |
| 5,588,432 A | * 12/1996 | Crowley | 600/374 |
| 5,620,479 A | 4/1997 | Diederich | 607/97 |
| 5,630,837 A | 5/1997 | Crowley | |
| 5,706,252 A | 1/1998 | Le Verrier et al. | |
| 5,720,287 A | * 2/1998 | Chapelon et al. | 600/439 |
| 5,733,315 A | 3/1998 | Burdette et al. | 607/97 |
| 5,976,090 A | 11/1999 | Hanafy et al. | |
| 6,050,943 A | 4/2000 | Slayton et al. | |
| 6,419,648 B1 | * 7/2002 | Vitek et al. | 601/3 |

FOREIGN PATENT DOCUMENTS

| | | | |
|---|---|---|---|
| EP | 0 351 610 A2 | 1/1990 | |
| EP | 0369 177 A2 | 5/1990 | |
| WO | WO 98/56462 | 12/1998 | A61N/7/02 |

OTHER PUBLICATIONS

Chen L, ter Haar G, Hill C R 1997 Influence of ablated tissue on the formation of high intensity focused ultrasound lesions *Ultrasound Med Biol* 23(6) 921–931.

Chopra R, Bronskill M J, Foster F S 2000 Feasibility of linear arrays for interstitial ultrasound thermal therapy *Med Phys* 27(6), 1281–1286.

(List continued on next page.)

*Primary Examiner*—Francis J. Jaworski
*Assistant Examiner*—Barry Pass
(74) *Attorney, Agent, or Firm*—Bereskin & Parr

(57) ABSTRACT

The present invention is directed to an imaging-compatible device for insertion into a region of tissue under image guidance, which employs ultrasound energy for the generation of thermal lesions. Coagulation can be confined to particular sectors in tissue through rotational control of the device. The depth of coagulation can be controlled through simultaneous modulation of the operating frequencies and powers. Described is a device which comprises a transducer located within a housing suitable for tissue insertion. The transducer comprises at least one piezoceramic element with at least one acoustic matching layer comprising a high acoustic impedance material for generating acoustic energy in narrow passbands around multiple resonant frequencies with high acoustic efficiency. The magnitude and frequency of the electrical power delivered to each element can be manipulated simultaneously providing control over the 3-dimensional shape of the thermal lesion created in tissue.

33 Claims, 11 Drawing Sheets

OTHER PUBLICATIONS

Chung A H, Hynynen K, Colucci V, Oshio K, Cline H E, Jolesz F A 1996 Optimization of spoiled gradient–echo phase imaging for in vivo localization of a focused ultrasound beam *Magn Reson Med* 36 745–752.

Damianou C, Hynynen K 1993 Focal spacing and near–field heating during pulsed high temperature ultrasound therapy *Ultrasound Med Biol* 19 777–787.

Damianou C A, Sanghvi N T, Fry F J, Maass–Moreno R 1997 Dependence of ultrasonic attenuation and absorption in dog soft tissues on temperature and thermal dose *J Acoust Soc Amer* 102 828–634.

De Poorter, J, De Wagter C, De Deene Y, Thomsen C, Stahlberg F, Achten E 1995 Noninvasive MRI thermomentry with the proton resonance frequency (PRF) method: in vivo results in human muscle *Magn Res Med* 33 74–81.

Deardorff D L, Diederich C J, Nau W H 1988 Air–cooling of direct–coupled ultrasound applicators for interstitial hyperthermia and thermal coagulation *Med Phys* 25(12) 2400–2409.

Dewey, W C, 1994 Arrhenius relationships from the molecule and cell to the clinic International Journal of Hyperthermia 10(4), 457–483.

Ebbini E S, Cain C A 1989 Multiple–Focus Ultrasound Phased Array Pattern Synthesis: Optimal Driving–Signal Distributions For Hyperthermia *IEEE Trans Ultrasom Ferroelect Freq Contr* 36(5) 540–548.

Fan X, Hynynen K, 1996 Ultrasound surgery using multiple sonications–treatment time considerations *Ultrasound Med Biol* 22(4) 471–482.

Hynynen K, Roemer R, Moros E, Johnson C, Anhalt D 1986 The effect of scanning speed on temperature and equivalent thermal exposure distributions during ultrasound hyperthermia in vivo *IEEE Trans Micro Theory Tech* MTT–34(5) 552–559.

Hynynen K, Freund W R, Cline H E, Chung A H, Watkins R D, Vetro J P, Jolesz F A 1996 A clinical, noninvasive, MR Imaging monitored ultrasound surgery method *RadioGraphics* 16 185–195.

Lafon C, Chapelon J Y, Prat F, Gorry F, Margonari J, Theillere Y, Cathignol D 1998 Design and preliminary results of an ultrasound applicator for interstitial thermal coagulation *Ultrasound Med Biol* 24(1) 113–122.

Lizzi F L, Astor M, Deng C, Rosado A, Coleman D J, Silverman R 1996 Asymmetric focussed arrays for ultrasonic tumor therapy *Proceedings IEEE Ultrasonics Symposium* 2 1281–1284.

Malcolm A L, ter Haar G R 1996 Ablation of tissue volumes using high intensity focused ultrasound *Ultrasound Med Biol* 22(5) 659–669.

McDannold N, Hynynen K, Wolf D, Wolf G, Jolesz F 1998 MRI evaluation of thermal ablation of tumors with focused ultrasound *J Magn Reson Imaging* 8(1):91–100.

Moros E G, Roemer R B, Hynynen K 1988 Simulations of scanned focused ultrasound hyperthermia: The effect of scanning speed and pattern on the temperature fluctuations at the focal depth *IEEE Trans Ultrasound Ferroelect Freq Contr* 35(5) 552–559.

Rivens I H, Clarke R L, ter Haar G R 1996 Design of focused ultrasound surgery transducers *IEEE Trans Ultrason Ferroelect Freq Contr* 43(6) 1023–1031.

Thomsen S, 1991 Pathologic analysis of photothermal and photomechanical effects of laser–tissue interactions. *Photochem. Photobiol*, 53(6), 825–835.

Zimmer J E, Hynynen K, He D S, Marcus F 1995 The feasibility of using ultrasound for cardiac ablation *IEEE Trans Biomed Eng* 42(9) 891–897.

Vykhodtseva N I, Hynynen K, Damianou C 1995 Histologic effects of high intensity pulsed ultrasound exposure with subharmonic emission in rabbit brain in vivo *Ultrasound Med. Biol* 21(7) 969–979.

Patrick J T, Nolting M N, Goss S A, Dines K A, Clendenon J L, Rea M A, Heimburger R F 1990 Ultrasound and the blood–brain barrier *Adv Exp Med Biol* 267 369–381.

Miller D L, Bao S, Morris J E 1999 Sonoporation of cultured cells in the rotating tube exposure system *Ultrasound Med. Biol* 25(1) 143–149.

Bao S, Thrall B D, Miller D L 1997 Transfection of a reporter plasmid into cultured cells by sonoporation in vitro *Ultrasound Med. Biol* 23(6) 953–959.

Vekris A, Maurange C, Moonen C, Mazurier F, De Verneuil H, Canioni P, Voisin P 2000 Control of transgene expression using local hyperthermia in combination with a heat–sensitive promoter *J. Gene Med* 2(2) 89–96.

Lawrie A, Brisken A F, Francis S E, Tayler D I, Chamberlain J, Crossman D C, Cumberland D C, Newman C M 1999 Ultrasound enhances reporter gene expression after transfection of vascular cells in vitro *Circulation* 99(20) 2617–2620.

Miller M W 2000 Gene transfection and drug delivery Ultrasound Med. Biol 26(1) S59–S62.

Kim H J, Greenleaf J F, Kinnick R R, Bronk J T, Bolander M E 1996 Ultrasound–mediated transfection of mammalian cells *Hum Gene Ther* 7(11) 1339–1346.

Deardorff D L, Diederich C J 1999 Angular directivity of thermal coagulatiion using air–cooled direct–coupled interstitial ultrasound applicators *Ultrasound in Medicine and Biology* 25(4) 609–622.

Lafon C, Chapelon J Y, Prat F, Gorry F, Theillere Y, Cathignol D 1998 Design and in vitro results of a high intensity ultrasound interstitial applicator *Ultrasonics* 36 683–687.

Diederich C J, Hynynen K 1999 Ultrasound Technology for Hyperthermia *Ultrasound in Medicine and Biology* 25(6) 871–887.

de Fraguier S, Gelly J F, Wolnerman L, Lannuzel O 1990 A Novel Acoustic Design for Dual Frequency Transducers Resulting in Separate Bandpass for Colour Flow Mapping (CFM) *Ultrasonics Symposium* 794–803.

Bolorforosh M S S 1992 Dual frequency piezoelectric transducer for medical applications *SPIE* 1733 131–140.

\* cited by examiner

A

B

C

X

TECHNIQUE AND APPARATUS FOR ULTRASOUND THERAPY

FIELD IF THE INVENTION

The present invention relates to the field of thermal therapy for treatment for various medical conditions, for example, tumors, and is concerned with ultrasound therapy, more particularly the devices and methods of use of such devices.

BACKGROUND OF THE INVENTION

Thermal therapy is a technique for the treatment of tumors in which heat is used to destroy cancerous tissue. It is a potential candidate for the treatment of solid, localized tumors in tissue. "Hyperthermia" refers to thermal therapies in which the target temperatures achieved in tissue are between 42 and 46° C. In this temperature region, the relationship between cell death, temperature and time is described by a thermal dose equation, and exposure times are typically between 30 and 60 minutes at 43–45° C. (Dewey, 1994). Thermal coagulation refers to thermal therapies in which target temperatures achieved in tissue are between 55 and 90° C. The application of temperatures in excess of 55° C. results in rapid destruction of tissue primarily through thermal coagulation. This higher temperature regime delivers sufficient energy to denature proteins and produces complete cell death in the treated region within a short time (seconds) (Thomsen, 1991).

The use of thermal coagulation for tissue destruction is predicated on effective guidance and monitoring of heat delivery. Real-time medical imaging plays an integral role, providing important information about anatomy, temperature, and tissue viability during and after the delivery of heat. This information can be used to target heat delivery to specific locations, monitor the amount of heat delivered, and assess the biological damage incurred, thereby eliminating the need to expose the treatment site to visual assessment. Monitoring the spatial delivery of heat with magnetic resonance imaging (MR) can avoid damage to critical structures and other normal tissue.

In interstitial thermal therapy, heat is produced by devices inserted directly into a target site within an organ. Potentially less invasive than conventional surgery, this approach can make possible the treatment of tumors in otherwise inaccessible locations. Several technologies have been employed for interstitial heating, including lasers, radio-frequency waves, and microwaves. These devices have been shown to be capable of generating temperature elevations sufficient for thermal coagulation of tissue. Some characteristics of these devices, however, limit their ability to treat large volumes or regions close to important anatomical structures. High temperatures (>90° C.) close to the device surface often leads to undesirable physical effects of charring or vaporization in tissue. Inadequate heating can occur at the target boundary due to rapid decreases in deposited power with increasing distance from the device. A common characteristic among existing interstitial devices is the shape of the spatial heating pattern, usually spherical or ellipsoidal. This property makes the treatment of asymmetrically shaped volumes of tissue difficult. The goal with interstitial thermal devices is to deliver a heating pattern which is as uniform as possible to the entire target volume of tissue, while avoiding excessive or inadequate heating.

The ability to generate rapid, localized temperature increases in tissue has led to the development of focused ultrasound as a method to treat tumors. Magnetic resonance (MR) imaging is well suited for use in conjunction with high intensity ultrasound as a means of treatment guidance and monitoring. MR-derived information can indicate beam position, tissue temperature, and can distinguish regions of thermal coagulation (McDannold et al., 1998; de Poorter et al., 1996; Chung et al., 1996). The feasibility of MRI-guided therapy with high intensity ultrasound has been demonstrated (Hynynen et al., 1996).

High intensity ultrasound treatment requires the coagulation of all the tissue within the tumor volume (Malcolm and ter Haar, 1996). In the case of a focused beam from an external transducer, multiple small lesions are placed throughout the target volume. For complete tumor coagulation, lesions must be closely spaced or overlapped, but gaps in coverage and unpredictable lesion formation can occur due to changes in the acoustic properties of heated tissue (Chen et al., 1997; Damianou et al., 1997).

A confounding factor, in the case of externally focused ultrasound is the heating of intervening tissue in the nearfield of the acoustic beam (Damianou and Hynynen, 1993). In the extreme case, this can result in burning of the skin (Rivens et al., 1996). To overcome this problem, sonications are separated by sufficient time for intervening areas to cool down, usually 1–2 minutes (Fan and Hynynen, 1996). This approach can reduce damage to intervening layers of tissue but treatment times become unacceptably long (1–2 hours). Transducer systems have, thus, been designed to coagulate larger volumes per sonication in an effort to reduce treatment times (Fjield et al., 1997; Ebbini and Cain, 1988; Lizzi et al., 1996, McGough et al., 1994).

A different approach is to use interstitial ultrasound heating applicators designed for insertion into tissue under image guidance, which deposit energy directly within a targeted region. The delivery of ultrasound is localized to the tumor, and the problem of heating intervening tissue layers is avoided. Interstitial transducers have been developed for a variety of applications including cardiac ablation (Zimmer et al., 1995), prostate cancer (Deardorff et al., 1998), and gastrointestinal coagulation (Lafon et al., 1998).

Scanning an acoustic beam permits the energy concentrated in the acoustic field to be distributed over a volume. This can result in more uniform heating of a larger region of tissue. The effects of scanning an acoustic beam for hyperthermia (Hynynen et al., 1986; Moros et al., 1988), and more recently for high intensity thermal coagulation (Chen et al., 1997) have been studied. At acoustic intensities sufficient for tissue coagulation, scanning generated continuous regions of thermal damage in excised liver specimens (Chen et al., 1997). This scanning technique is unsuitable for external ultrasound therapy due to excess nearfield heating, but is potentially well advantageous for interstitial ultrasound heating.

The main limitation with current interstitial devices is the output power of the transducers, due to their small size. High power is required to generate thermal coagulation in tissue within a reasonable time with a scanned acoustic beam. Effects of local blood flow could result in incomplete thermal coagulation if insufficient power is generated. With adequate power, however, the potential exists for the coagulation of large regions of tissue with interstitial ultrasound for treatment of tumors.

The theoretical heating patterns of single element and linear array transducers has been investigated in a previous study by Chopra et al. (2000). These calculations indicated the differences in the heating patterns from the two transducer designs, and highlighted the importance of achieving a high output acoustic power. However, there is a continuing need for a heating device which is able to deliver a uniform heating pattern to a target volume of tissue.

SUMMARY OF THE INVENTION

The present invention overcomes limitations of the prior art by providing an ultrasound heating applicator for thermal therapy of tissue. Preferably, an applicator according to the invention is compatible with imaging, more preferably MR imaging. Such an applicator is also preferably compatible with image-guided interstitial therapy, preferably of benign or malignant tissues. In its broad aspect the interstitial ultrasound applicator of the present invention is comprised of a transducer, preferably planar, with multiple acoustic matching layers enabling operation at a range of frequencies for optimal "control" of the depth of thermal coagulation.

In an embodiment of the present invention, an applicator has the capability for varying the frequency of each individual element thereby enabling the tissue temperature to be adjusted both radially and along the length of the applicator or catheter. This provides critical adjustability for accommodating irregular tumor geometry, heterogeneities of the tissue thermal properties, and dynamic changes in perfusion. In addition, the heat deposition pattern is not significantly dependent on the length of insertion or placement of the device with regard to the target or other devices in the implant.

Accordingly, the present invention provides a device for thermal coagulation of tissue comprising:
(a) a multifrequency ultrasound transducer for providing acoustic energy at multiple discrete frequencies, the transducer having at least one matching layer comprising a high acoustic impedance material having an acoustic impedance comparable to the acoustic impedance of the transducer for generating acoustic energy at discrete frequencies with high efficiency of acoustic energy transmission;
(b) a housing for the transducer;
(c) means for delivery of variable frequency and power to the transducer; and,
(d) an acoustic window. Preferably the device further comprises a motor control system and means to control frequency and power of ultrasound simultaneously and independently, wherein the motor control system provides rotational control of the device to isolate heating to parts of tissue, means to control frequency and power allow for adjustment of the depth of thermal coagulation. Preferably the transducer of a device of the invention is a multiple element transducer with at least one matching layer.

In another embodiment the transducer is a multi-element transducer with individual elements between about 6–20 wavelengths in length, each of which comprises one or more matching layers.

In yet another embodiment the transducer is a phased array transducer, with elements less than about 1 wavelength in length.

In another embodiment according to the present invention there is provided a device according to the embodiments described wherein at least three transducers are incorporated into the device wherein at least one of each of which comprises:
(a) a single element transducer with multiple matching layers;
(b) a multi-element transducer with individual elements between about 6–20 wavelengths in length; or
(c) a phased array transducer with less than about 1 wavelength in length.

In an embodiment of the present invention the transducer(s) are capable of delivering ultrasound energy at efficiencies over a range of frequencies spanning approximately 70% fractional bandwidth, preferably the transducer(s) is(are) comprised of a ¼ wavelength front matching layer of a high acoustic impedance material, capable of delivery of acoustic energy at two discrete frequencies. In another embodiment the transducer(s) is(are) comprised of a ½ wavelength front matching layer of high acoustic impedance material, capable of delivery of acoustic energy at three discrete frequencies.

In yet another embodiment of a device according to the present invention the transducer material is PZT.

In still a further embodiment, a device according to the invention is constructed of MR-compatible materials chosen from a metal, ceramic or a polymer, preferably the material is a metal and is brass, copper, or stainless steel. More preferably, where the material is a polymer it is Poly(ether ether ketone)PEEK.

In another embodiment the housing of a device according to the present invention further comprises a tube means for infusing a therapeutic agent into a patient.

In yet another embodiment a device according to the present invention further comprises an acoustically transparent catheter.

In another aspect of the present invention there are provided various methods which incorporate a device of the invention. Accordingly, in one embodiment the present invention provides a method for interstitial ultrasound thermal therapy of tissue comprising:
(a) determining the target tissue volume from images;
(b) planning a route of insertion for a device and a heating regime based on the images, the heating regime comprising a sequence of scan rates, transmission frequencies and powers as a function of device angle;
(c) inserting the device into a desired location for the interstitial thermal coagulation of the target tissue volume, the device comprising a multifrequency ultrasound transducer for providing acoustic energy at multiple discrete frequencies with high efficiency, the transducer having at least one matching layer comprising a high acoustic impedance material;
(d) implementing the heating regime by delivering the acoustic energy to the target tissue volume from the device, the acoustic energy having various frequencies selected from the multiple discrete frequencies, and by rotating and translating the device for producing a thermal lesion conformal to the target tissue volume; and
(e) assessing the thermal lesion with imaging.

In yet another embodiment, the present invention provides a method: of delivering high intensity sound pulses for the purposes of activating either sonically or thermally a therapeutic agent to deliver therapy comprising:
(a) determination of the target tissue volume from images;
(b) planning route of insertion and heating regiment based on the images;
(c) insertion of a device according to claim 2 for the interstitial thermal coagulation of tissue into a desired location in tissue;
(d) delivery of heat with continued monitoring of temperature distribution around said device; and
(e) assessment of the efficacy of activation.

Preferably the transducer of these embodiments of methods of the invention is a single element transducer with multiple matching layers.

In another embodiment the transducer is a multi-element transducer with individual elements between about 6–20 wavelengths in length, each of which comprises one or more matching layers.

In yet another embodiment the transducer is a phased array transducer, with elements less than about 1 wavelength in length.

In another embodiment according to the methods of the present invention there is provided a device, according to the embodiments of the device, wherein at least three transducers are incorporated into the device wherein at least one of each of which comprises:

(a) a single element transducer with multiple matching layers;

(b) a multi-element transducer with individual elements between about 6–20 wavelengths in length; or (c) a phased array transducer with less than about 1 wavelength in length.

In an embodiment of the methods of present invention the transducer(s) used in the methods are capable of delivering ultrasound energy at efficiencies over a range of frequencies spanning approximately 70% fractional bandwidth, preferably the transducer(s) is(are) comprised of a ¼ wavelength front matching layer of a high acoustic impedance material, capable of delivery of acoustic energy at two discrete frequencies. In other embodiments of the methods the transducer(s) is(are) comprised of a ½ wavelength front matching layer of high acoustic impedance material, capable of delivery of acoustic energy at three discrete frequencies.

In yet another embodiment of the methods the transducer material of a device according to the present invention is PZT.

In still a further embodiment of the methods, a device used in the methods is constructed of MR-compatible materials chosen from a metal, ceramic or a polymer, preferably the material is a metal and is brass, copper, or stainless steel. More preferably, where the material is a polymer it is Poly(ether ether ketone)PEEK.

In another embodiment of the methods, the housing of a device according to the present invention, as used in the methods, further comprises a tube means for infusing a therapeutic agent into a patient.

In yet another embodiment, a device used in the methods further comprises an acoustically transparent catheter.

Other features and advantages of the present invention will become apparent from the following detailed description. It should be understood, however, that the detailed description and the specific examples while indicating preferred embodiments of the invention are given by way of illustration only. Various changes and modifications within the spirit and scope of the invention will become apparent to those skilled in the art from this detailed description.

BRIEF DESCRIPTION OF THE DRAWINGS

The following figures describe the nature of the proposed device, in order to clarify its design and application for thermal therapy.

DETAILED DESCRIPTION OF THE INVENTION

Figure 1:
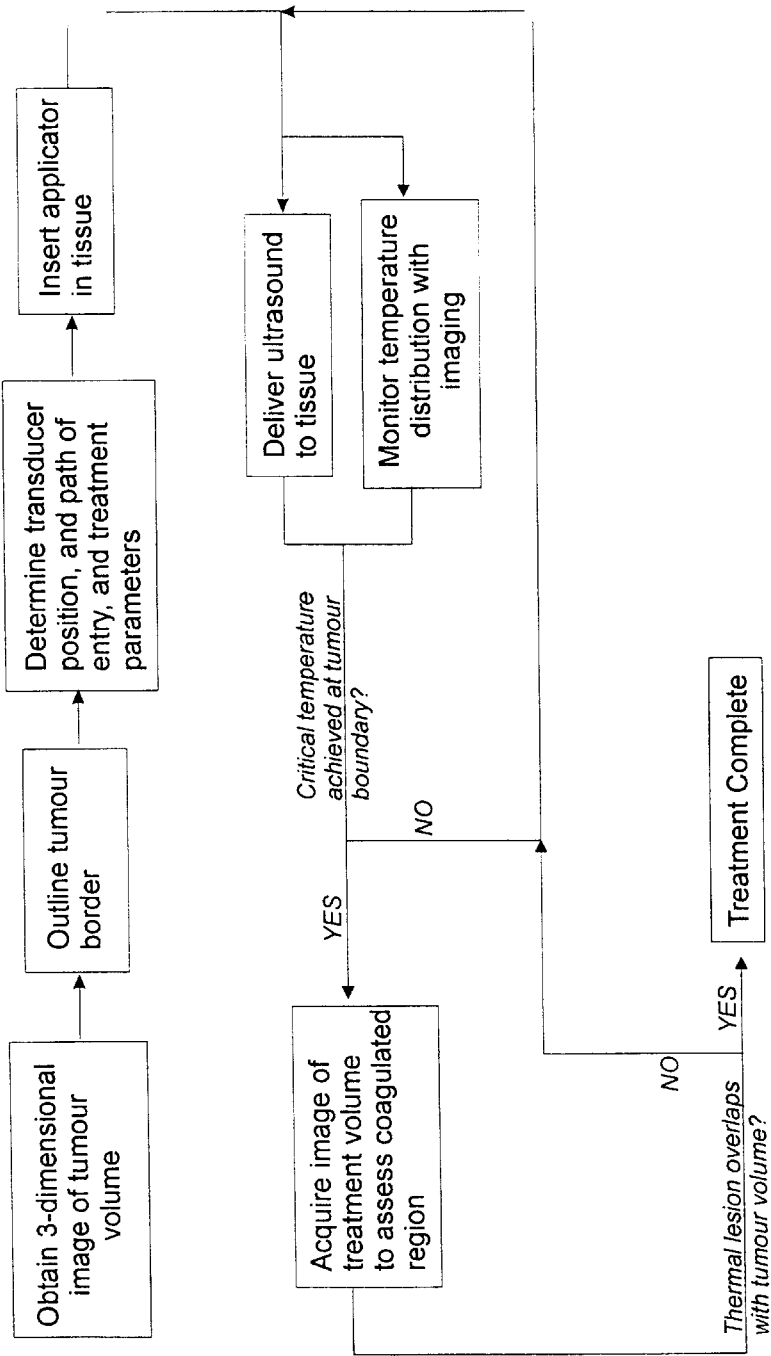
FIG. 1 is a flow diagram illustrating the method of image-guided interstitial coagulation of tumors.

As mentioned above, the present inventors have developed an ultrasound heating applicator for therapy of tissue. In addition an embodiment of an applicator of the invention is compatible with imaging.

As used herein, the expressions "heating applicator" and "applicator" mean the device used to conduct thermal therapy and which is the subject of the present specification.

As used herein, the expression "scan" means the energy from a applicator transmitted over a region of tissue as achieved through movement of a applicator of the invention, where the movement may include periods of no movement, combined with movement, or continuous movement.

As used herein, the expression "transducer" means one or more elements capable of emitting ultrasound.

Heating Applicator

In its broad aspect a device according to the present invention is an interstitial ultrasound applicator comprised of a transducer with multiple acoustic matching layers enabling operation at a range of frequencies for optimal control of the depth of thermal coagulation. In an embodiment, the range of frequencies may be delivered simultaneously from the same transducer or different frequencies may be delivered from different elements of a transducer. The transducer shape can be oval, planar, semi-circular, octagonal, hexagonal or any polygon or shape. According to one embodiment, the device is seated in a housing, preferably a tubular housing, more preferably the housing is rigid. A temperature control system is also available where the coolant is used to control the temperature of the transducer. Such use of the coolant may heat or cool the immediately adjacent tissue. Preferably, local temperature control is achieved by having water flowing across the surface of the device.

The transducer may be a single element, multi-element transducer, or a phased array, depending on the requirements on the accuracy and control over the spatial pattern of heating. The operating frequency range for these transducers is typically between 2 and 10 MHz, and between 10 and 40 W of electrical power is delivered to the device during heating. The generation of a conformal heating pattern is possible through rotational control of the applicator, and control over the radial and axial depth of thermal coagulation. These characteristics result in the ability to prescribe and deliver a three-dimensional pattern of thermal coagulation in tissue.

The heating applicator is designed to be used in conjunction with any type of imaging device including MRI, ultrasound or any device which is able to allow the imaging of a applicator of the invention, in other words, that makes the applicator visible and includes CT scans. MR imaging can be used to define the target tumor and surrounding anatomical structures, ultimately guiding the insertion path and approach of the device. Rapid imaging, accomplished with MRI and/or ultrasound can guide the device during insertion to ensure that correct placement is achieved. During the delivery of ultrasound to tissue, MR can non-invasively measure the temperature distribution in the region of tissue around the heating applicator to ensure that excessive heating is avoided close to the applicator, and adequate heating occurs at the treatment boundary. Finally, upon completion of treatment, MR images sensitive to thermal damage of tissue, such as T2-weighted and/or contrast-enhanced T1-weighted images can be acquired of the treatment volume to assess the extent of thermal coagulation.

The design of a preferred embodiment of an applicator according to the present invention is for the delivery of high intensity ultrasound to a tumor. Temperatures exceeding 55° C. are achieved in the tumor volume. To achieve such rapid heating, high power is preferably delivered to the ultrasound transducer, and according to one embodiment, water cooling is employed in order to remove any thermal losses. As will be appreciated by those skilled in the art, alternative means such as other cooling liquids, air or variety of gases, may be employed to remove such thermal losses. Since, in a preferred embodiment, a planar transducer is employed, the ultrasound field according to this embodiment is highly collimated, and the delivery of energy is highly localized. This allows for the coagulation of very small volumes of tissue. If larger volumes of coagulation are desired, the device can be rotated to spread the energy delivery over a larger volume. With this technique, arbitrary continuous sectors, multiple contiguous sectors, or alternatively arbitrary angular sectors of thermal coagulation can be generated. The nature of sectors generated will depend on the tissue under consideration and the location of other structures which must be avoided. The depth of coagulation at a given angular position is controlled by the choice of the ultrasound frequency delivered to tissue, and the magnitude of the power delivered. The simultaneous adjustment of these parameters which is possible with an applicator of the invention, enables precise control over the shape of the thermal lesion parallel and transverse to the heating applicator.

In the axial direction, the type of transducer determines the amount of control offered over the heating pattern. A single element transducer has a relatively uniform field pattern along the axis (for lengths greater than 10–20 lambda); thus, the control over the axial field pattern is limited. This type of heating is suitable for the generation of large heating patterns in situations where high accuracy of the placement of thermal lesions is not required. To improve control over the heating pattern in the axial dimension, the transducer can be divided into multiple elements (greater than 6–10 lambda). These elements can be operated independently and/or simultaneously at independent powers and frequencies, thereby enabling control over the depth of coagulation along this dimension. The heating pattern can be shaped according to the tumor geometry, and three dimensional control over the shape of the thermal lesion is achieved. For the maximum amount of control, such as in situations where small volumes of tissue are targeted for ablation (cardiac ablation, neurological disorders) a phased array transducer can be implemented. The advantage of the phased array is that the power distribution from the transducer can be controlled, and energy can be concentrated in a focal zone away from the surface of the applicator. This can result in the rapid coagulation of volumes of tissue of the order of a few $mm^3$ in dimension, with well defined boundaries. In general, the delivery of maximum power away from the applicator surface also enables the generation of more uniform temperature distributions, and larger depths of coagulation. Accordingly, control over the axial depth includes at least three approaches. The first is through "steering" or direction of the focal point of an array of elements. The second is through varying frequency and/or power along the length of the applicator and, third, adjusting the applicator's actual depth in the tissue under treatment.

For the multi-element, and phased-array designs, individual elements can serve multiple functions as both high power therapy and diagnostic transducers. Ultrasound images of a treatment region can be made before or after delivery of high intensity ultrasound to localize the beam to the appropriate location, and to assess the effect of the therapy.

An MR-compatible design of the applicator makes possible the use of MR thermometry during heating, to monitor the spatial delivery of heat. Proper selection of construction materials can result in minimal imaging artefacts, and temperature measurements can be made very close to the applicator surface. The use of thermometry in conjunction with interstitial heating improves the accuracy and control over heat delivery and can identify areas of excessive/inadequate heating.

Figure 2:
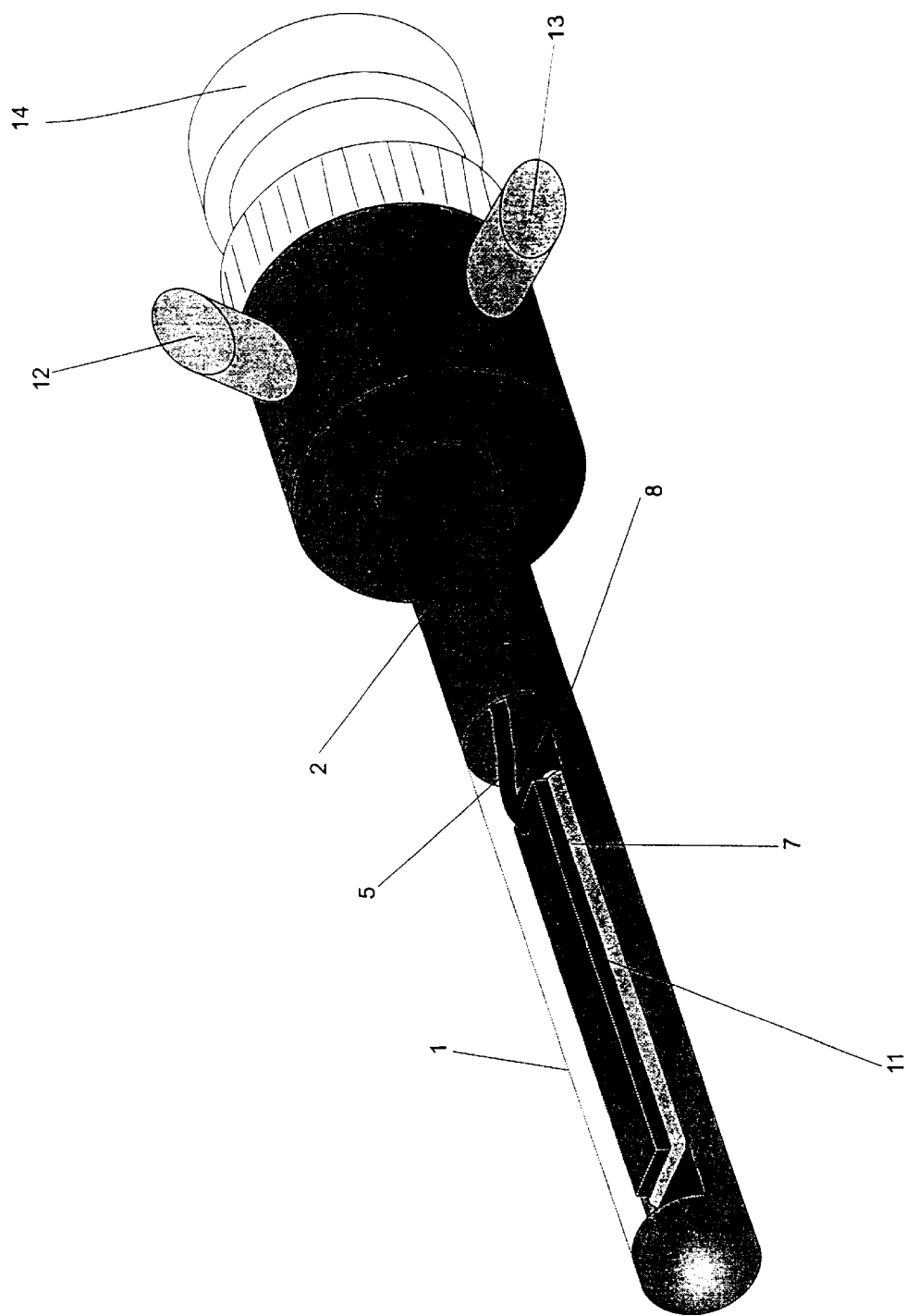
FIG. 2 is a three dimensional view of an embodiment of a heating applicator of the present invention.

The three-dimensional appearance of a preferred heating applicator according to the invention is shown in FIG. 2. The cylindrical applicator housing (2) is made of an MR compatible material such as ceramic, or metal such as brass or copper, plastics or a carbon fiber composite. The outer diameter of the applicator housing is preferably less than 5 mm in size. Part of the wall of the applicator housing is removed and replaced with any means to allow ultrasound energy to propagate into tissue, for example a thin polymer film (1). The tip of the device can be blunt, rounded, or sharpened, or any other configuration depending on the method of insertion into tissue. The location of the transducer (11) is close to the end of the applicator reducing the need to insert the device beyond the target tumor, however, as is readily apparent to a person skilled in the art, the location of the transducer is not critical; it is important only that it be placed in the applicator at a position that can allow for efficient delivery of energy to the target tissue, indeed, the transducer may move up and down the applicator and need not be fixed in any one position on the applicator. The transducer is seated on a structural support (8) within the tubing, and is sealed in place with any adhesive or fixing means including, for example epoxy (7). The electrical power to the transducer is delivered through miniature cables (5), which are connected to the electrodes on either face of the transducer, although any means to deliver power to the transducer is within the scope of the invention. Coolant flows into the heating applicator via a port (12) located near the back of the applicator, and out from a nearby port (13). The electrical supply from an RF amplifier is connected to the heating applicator via a connector at the back end of the device (14).

Figure 3:
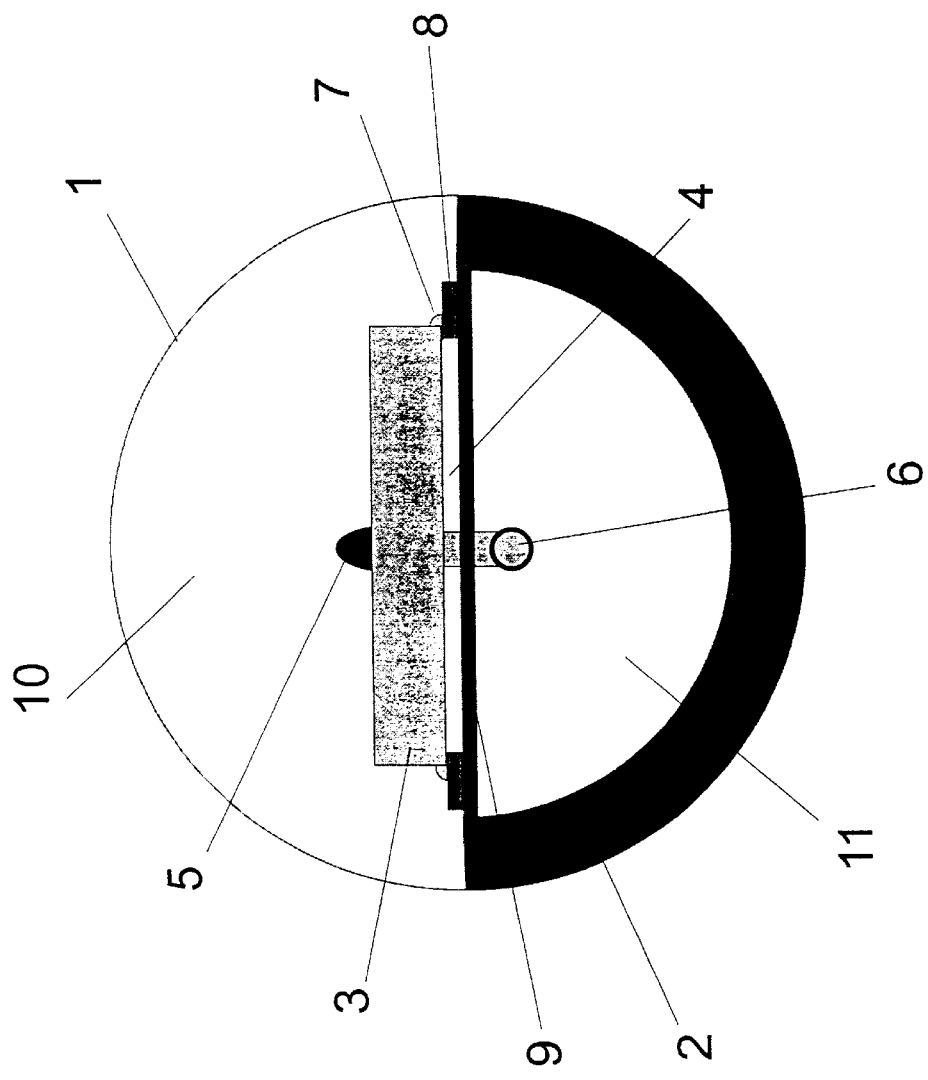
FIG. 3 is a transverse cross-section through the heating applicator of FIG. 2 at the location of the transducer showing the mechanical structure, electrical and cooling supply.

A more detailed view of some structural components of a applicator according to the present invention are shown in FIG. 3. The applicator housing (2) and the polymer film (1) acoustic window are depicted in FIG. 3. The applicator is divided into 2 equal volumes by a wall (9) passing through the entire length of the tubing. The top volume (10) acts as the water inflow channel for transducer cooling, while the bottom volume (11) acts as the water return. The transducer (3) sits slightly elevated above the dividing wall, leaving an air space (4) to ensure the transducer is airbacked. The air space is made water-tight by means of an epoxy seal (7) around the transducer. The signal wire (6) passes down the bottom volume and eventually passes through the dividing wall to connect with the transducer. The ground wire (5) passes through the top volume and is connected to the top electrode of the transducer. According to one embodiment, the entire applicator housing (2) may be metallized to provide electrical shielding of RF signals to reduce any possible interference with the MR-imaging system. However, as will be appreciated by a person skilled in the art, the entire applicator need not be metallized, i.e., only a portion thereof may be metallized. It may be, metallized with, for example, ceramic or a carbon fiber composite or a plastic polymer, for example Poly(ether ether ketone).

Figure 4:
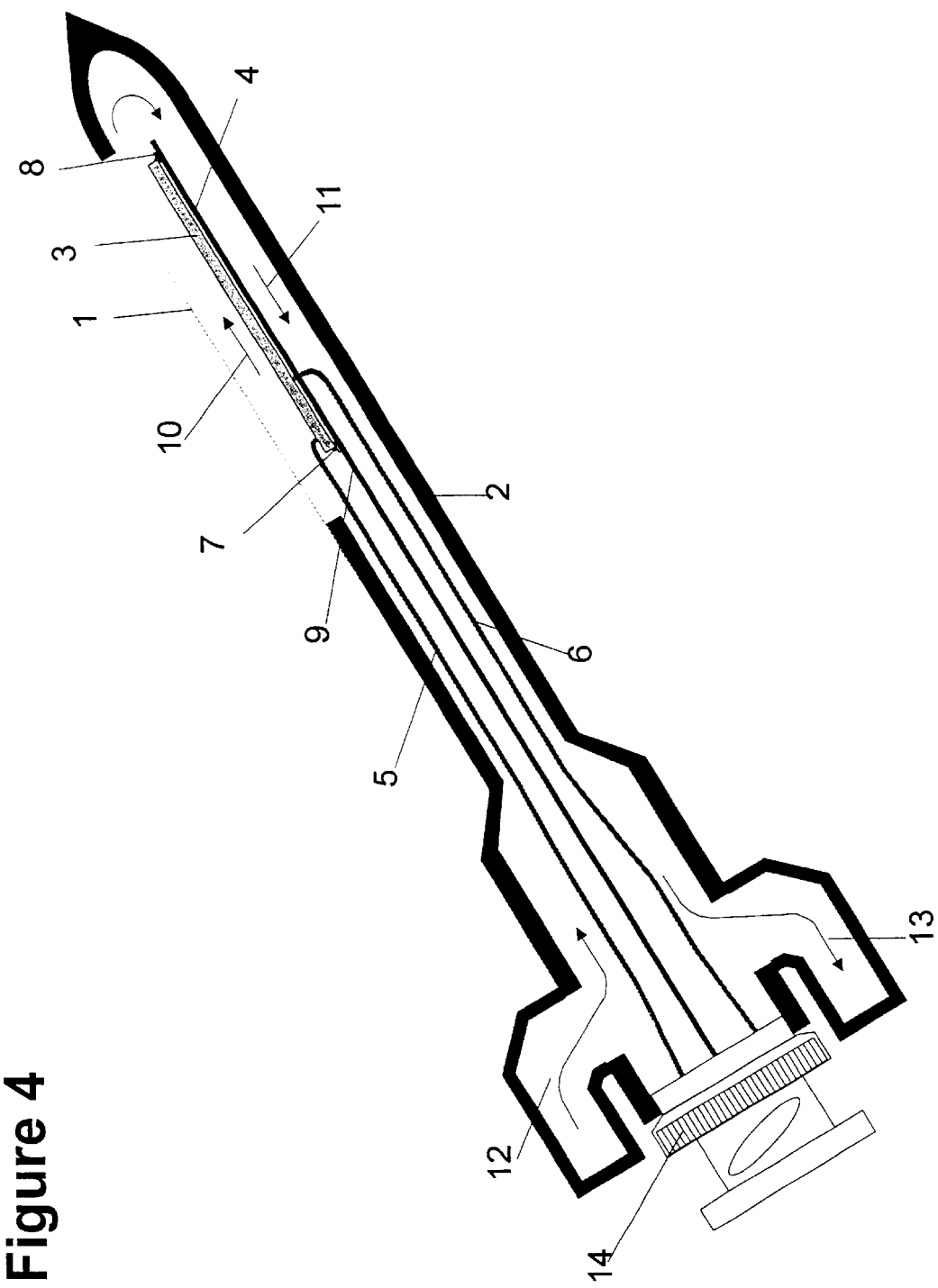
FIG. 4 is an axial cross-section through the heating applicator of FIG. 2 at the location of the transducer.

An axial cross-sectional view is presented in FIG. 4. The applicator housing.(2) can be seen, along with the exposed wall covered with a polymer film (1). The dividing wall (9) can be seen extending down the length of the applicator lumen. The ground wire (5) passes down the top half of the applicator, while the signal wire passes along the bottom half. Both wires connect to the transducer. The support steps (8) and the air space (4) below the transducer are seen in the figure. The arrows (10,11) in the figure depict the direction of water flow acting as coolant for the transducer. The front of the device is depicted with a sharp point suitable for direct penetration and insertion into tissue. Note that in this configuration the transducer is located close to the tip of the device.

Perforations or ports may be added to a applicator of the invention to inject, chemotherapeutic or other drugs which are activated either thermally (e.g., heat activated liposomes) or sonically.

Figure 5:
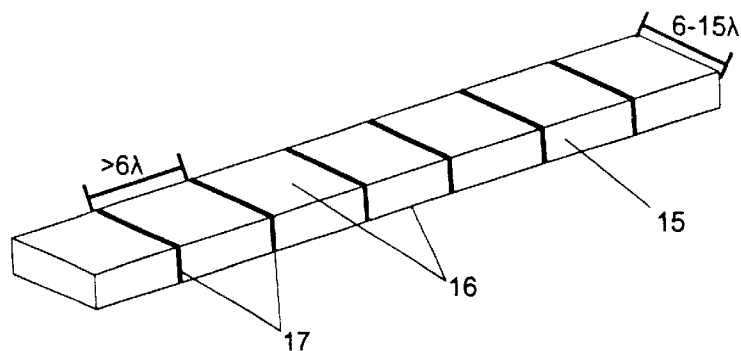
FIG. 5 illustrates possible transducer configurations for a heating applicator of the present invention.
Figure 5:
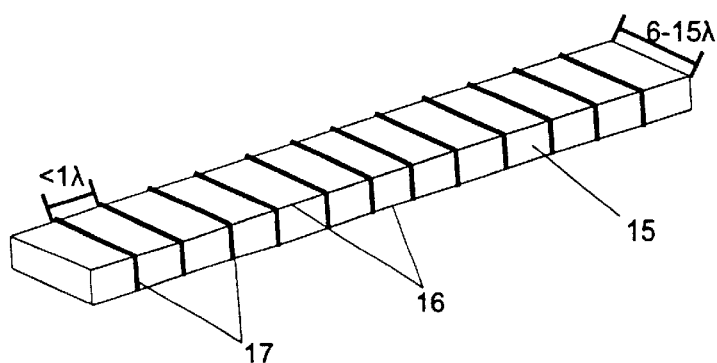
Figure 5:
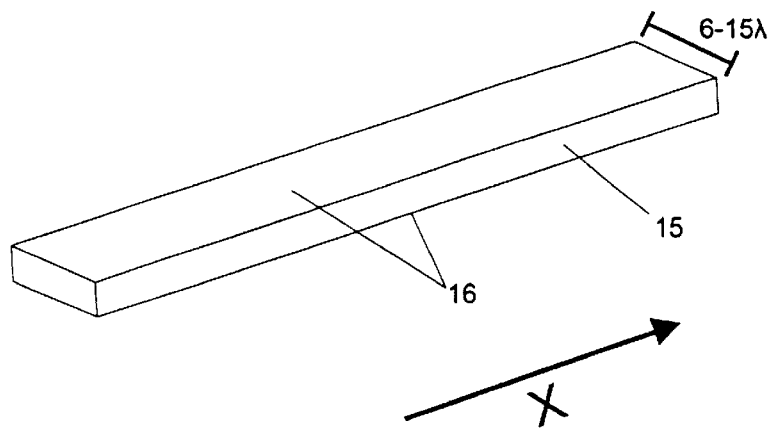

The possible configurations of transducer are shown in FIG. 5. Each configuration has unique heating properties and capabilities. The configuration in A is called a multi-element transducer and consists of individual elements (15), greater than 6 wavelengths in the x direction. The elements are separated by an epoxy kerf (17) and there are electrodes on both surfaces (16) of the transducer. In this configuration the frequency and power of each element can be controlled independently and/or simultaneously, enabling axial control over the shape of the heating pattern. Elements of this size cannot create interference patterns with each other, and therefore act as independent transducers. The configuration shown in B is called a linear array transducer. In this configuration, the elements of the transducer are less than a wavelength in the x-direction, and are separated by an epoxy kerf (17). The ability to dynamically focus the ultrasound field is possible with elements of this size, and this design can be used to create a highly localized region of heating which can be steered electronically. The simplest transducer design is shown in C, called a single element transducer. The acoustic field of this transducer is dependent on the operating frequency, and control over the axial field depends on device placement.

Figure 6:
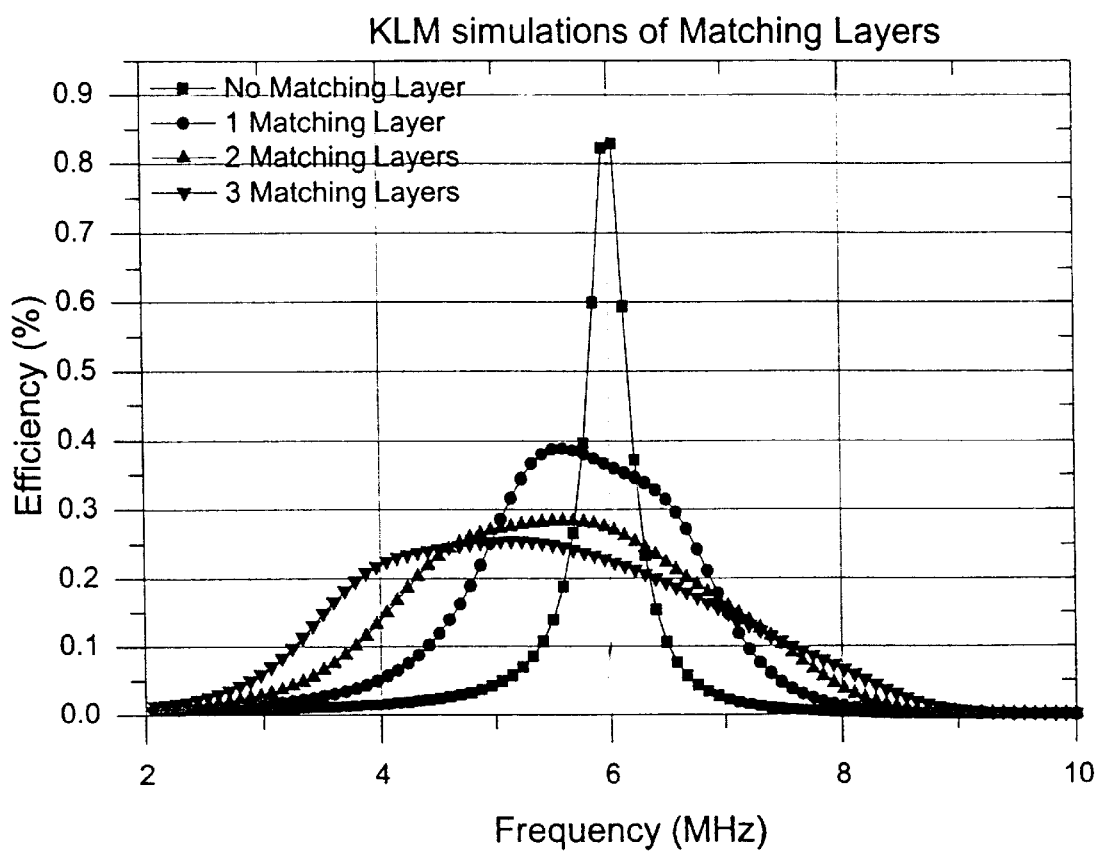
FIG. 6 shows increased power transmission bandwidth available for transducers of the invention with multiple matching layers.

The effects of acoustic matching layers on the transmission bandwidth of interstitial transducers is shown in FIG. 6. The graph depicts the transmission efficiency, defined as the ratio of the output power to the input power, over a range of frequencies. The calculations were performed by KLM modeling of the interstitial transducers. The center frequency of the transducer was set as 6 MHz, and the matching layers were each ¼ wavelength thick. Defining the bandwidth as the ratio of the full-width at half maximum of the curve to the center frequency (6 MHz), the following results were obtained. A bandwidth of 37% is obtained with 1 matching layer; 55% with 2 matching layers, and 69% with 3 matching layers, compared with a 7% bandwidth available for a transducer with no matching layers. There is a slight reduction in the maximum efficiency as the number of matching layers in increased. However, the addition of the matching layers enables heat delivery in tissue over a wide range of frequencies. The ability to control the frequency of ultrasound over a wide range during heating is a simple method by which the penetration depth can be controlled.

Figure 8:
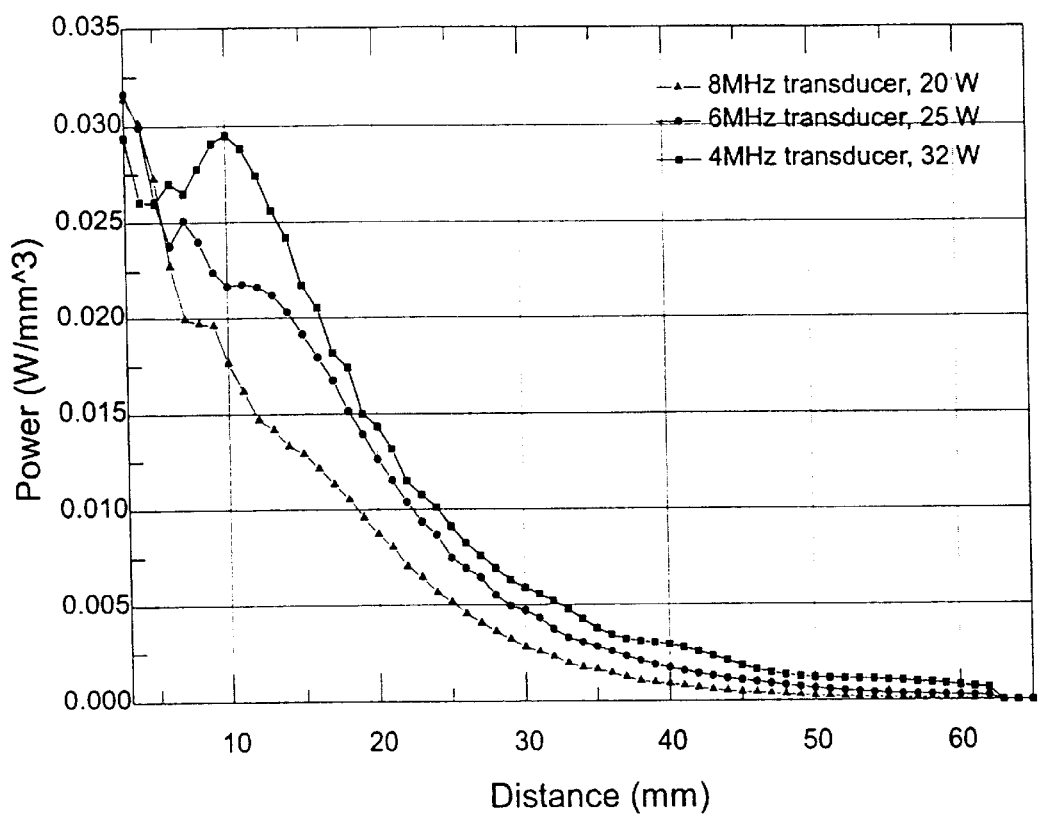
FIG. 8 is a graph of the transverse power distribution emitted from a transducer surface of the invention for 4, 6 and 8 MHz fields.

The radial acoustic power distribution for a single element transducer operating at 4, 6, or 8 MHz is shown in FIG. 8. The rapid drop in power with radial distance seen with the 8 MHz power distribution makes this frequency suitable for short range, rapid heating. The 4 MHz distribution is well suited for deeper heating due to the increased penetration of power. Note also that the electrical power delivery, shown in the legend of the figure, is different for each transducer. This is due to the fact that the absorption of power increases with frequency, and this must be compensated for in order to compare the power distributions equally. A transducer with 3 matching layers, and a center frequency of 6 MHz, would be able to deliver ultrasound energy from 4 to 8 MHz, making this kind of control over the power distribution from a single transducer possible.

Figure 7:
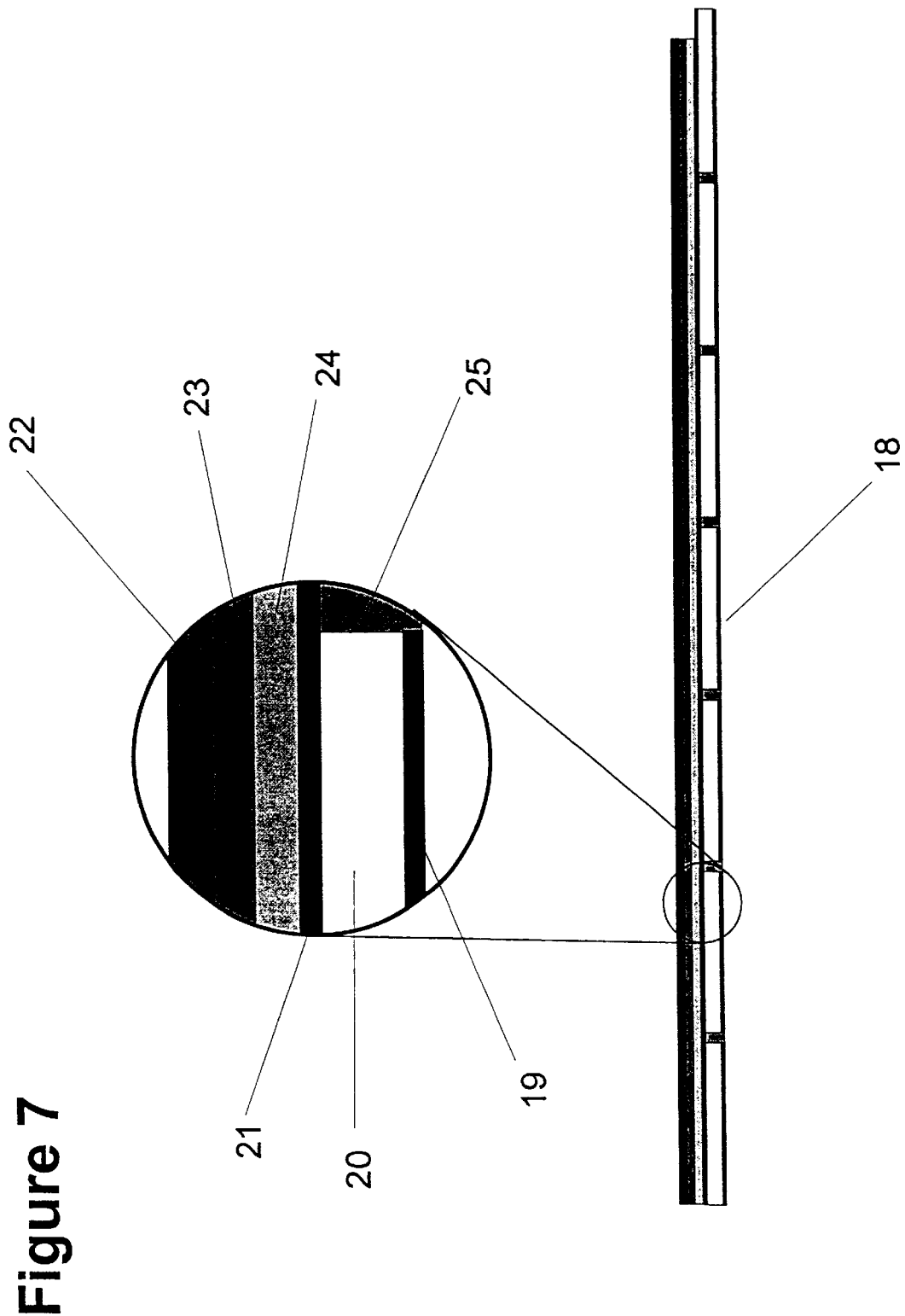
FIG. 7 is a cross-sectional view of transducer according to the invention showing matching layers and piezoceramic.

A cross-sectional view of a multi-layer transducer, shown with 3 front layers, is shown in FIG. 7. The relative size and position of the transducer elements (18), the electrode (19), and the matching layers (22–24) are shown in the figure and the inset.

Figure 9:
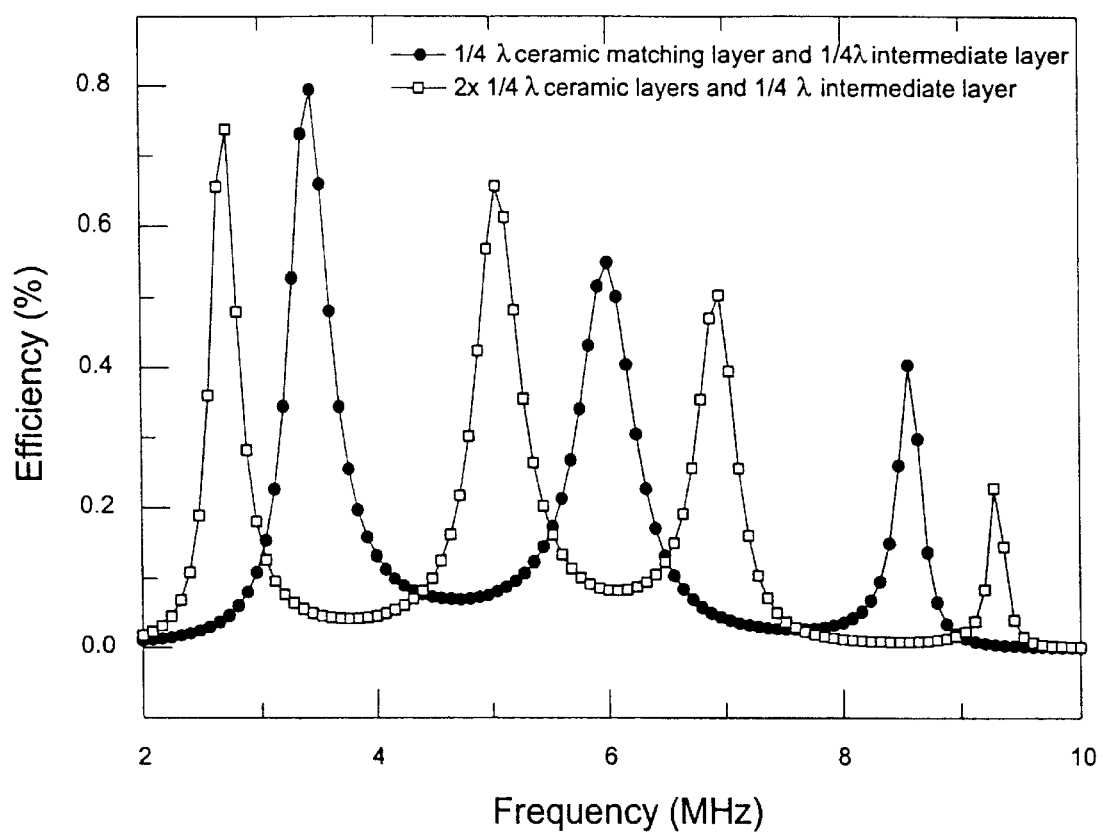
FIG. 9 shows the predicted power transmission bandwidth for multilayer transducers with various configurations of ceramic matching layers.

The predicted transmission spectrum for transducers with multiple high impedance matching layers is shown in FIG. 9. In both transducers, multiple quarter wavelength layers of ceramics are used to create discrete passbands of high efficiency acoustic transmission. The results of FIG. 9 demonstrate that appropriate choice of the layers can result in a transducer with 3 or 4 transmission bands.

Figure 10:
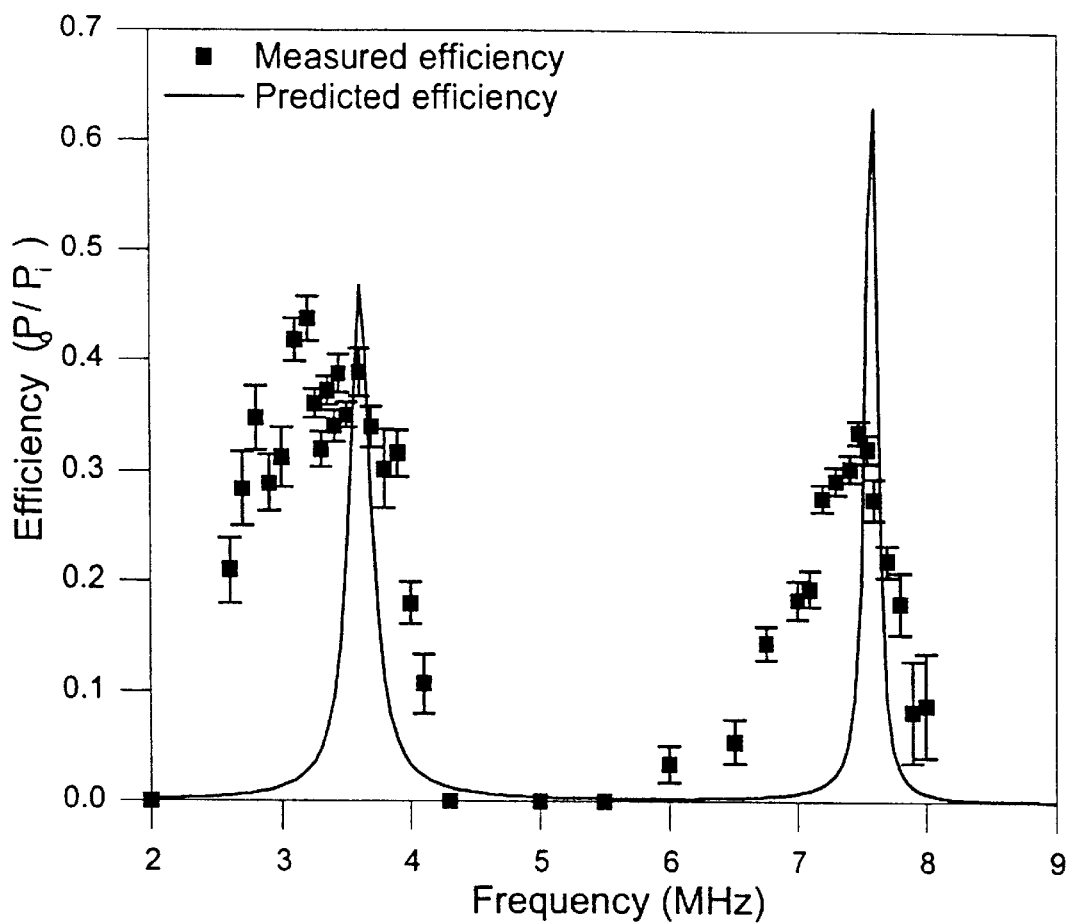
FIG. 10 shows the calculated and measured power transmission band width for a transducer of the invention with one ¼λ ceramic matching layer.
Figure 11:
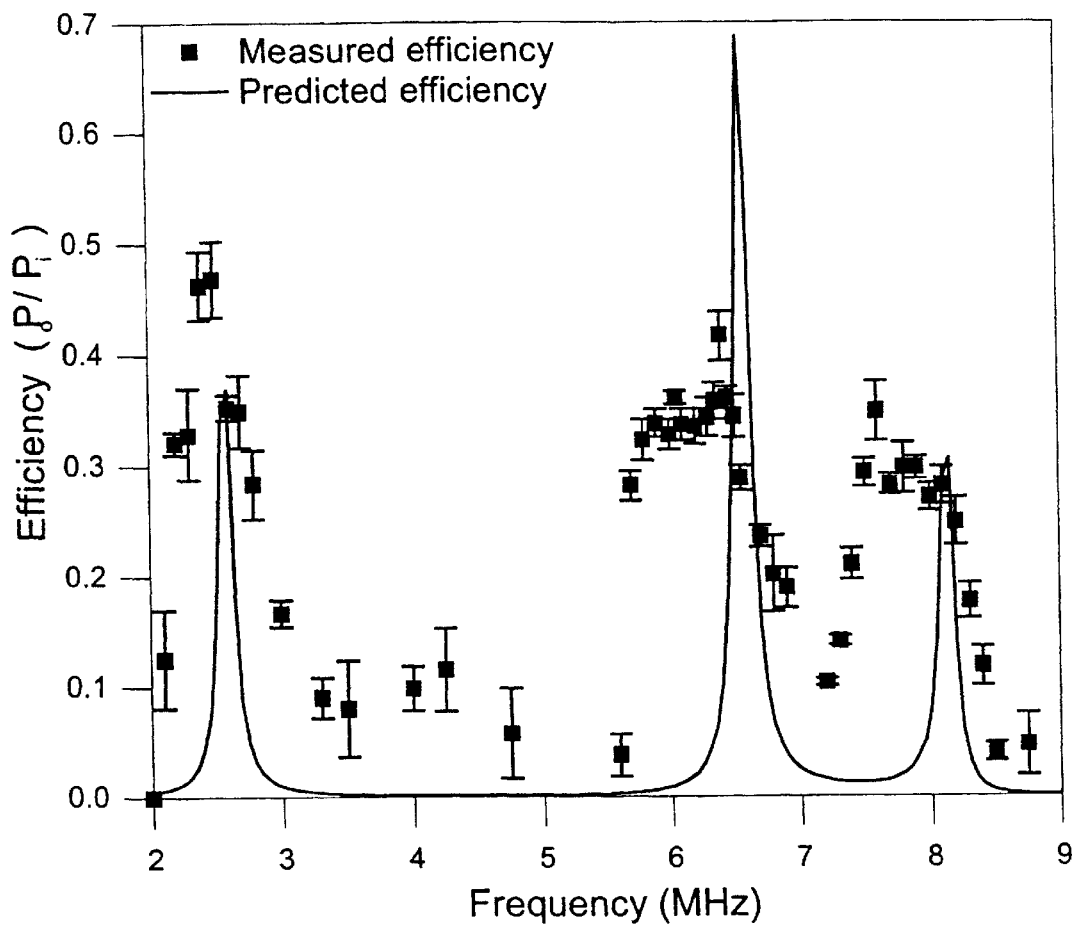
FIG. 11 shows the calculated and measured power transmission bandwidth for an interstitial transducer according to the invention with one ½λ ceramic matching layer.

A unique transmission bandwidth can be achieved through the application of a ¼ wavelength layer of a material with high acoustic impedance, for example ceramic. The bandwidth achieved with 1 ceramic matching layer is shown in FIG. 10. The KLM model was used to predict the performance of transducers with various front matching approaches, and experimental measurements from prototype transducers were performed to confirm predictions. In the case of 1 ceramic 2 distinct frequencies of transmission are possible, one at 3.5 MHz, and one at 7.5 MHz. Even more frequencies of transmission can be created by adding additional layers of ¼ wavelength thick ceramic to the transducer. Calculations of the transmission bandwidth for transducers incorporating 2 ceramic matching layers are shown in FIG. 11. The figure shows that 3 discrete bandwidths for transmission are achieved with this design of transducer. The resonant frequency of the transducer was measured to be 6.5 MHz prior to the addition of the front layers. The bandwidth of transmission at each of these frequencies is narrow, but the efficiency is high. This makes possible a single applicator with the ability to deliver ultrasound at multiple frequencies with high electrical efficiency for increased control over the depth of thermal lesion.

Methods of Thermal Therapy

The envisioned technique for image-guided interstitial ultrasound coagulation of tumors is outlined in FIG. 1. Prior to treatment, a 3 dimensional image data set is acquired to define the tumor volume, and the surrounding anatomy of interest. Treatment planning software outlines the borders of the tumor volume, based on the acquired images. This information is then used to determine the insertion path of the transducer, the final position of the device, and the scanning and operating parameters necessary to coagulate all the tissue within the treatment volume, while sparing surrounding normal tissue. The location of the device is flexible, and it can be inserted within, or adjacent to the target volume of tissue. The guidance of the device insertion is aided with rapid imaging, for example MRI, US or CT, to ensure the proper location of the device. Once the device has been inserted into the desired location in tissue, ultrasound energy is delivered and the appropriate movement and/or motion(s), frequency and/or power delivery of the applicator are undertaken. All of this therapy can be accomplished with one applicator of the invention inserted at one location. Alternatively, if other therapies are planned during the intervention, an acoustically transparent catheter can be inserted first, acting as a guide for the insertion of the heating applicator.

During treatment, images are continuously acquired to indicate the temperature distribution in the region of the applicator, for example with MRI. This information is used to ensure adequate heating at the tumor borders, and to avoid overheating near the transducer surface. This continues until the temperature at the treatment margins exceeds a critical temperature sufficient for thermal coagulation in tissue. Once this stop-point is reached, images sensitive to thermal damage, for example T2-weighted MR images, or contrast enhance T1-weighted images, are acquired to evaluate the extent of the thermal lesion. This serves as a confirmation of the damage pattern predicted by thermometry, and further heating can be performed if necessary. If the thermal lesion covers the entire tumor volume, then the treatment is completed, and the applicator is removed. Imaging of the treatment volume after treatment can be done to follow the progress of the treated region. At this point, if a catheter was initially inserted into the tumor, other therapies/diagnosis can be executed after the removal of the heating applicator from the catheter.

Insertion of a applicator according to the present invention into tissue can be accomplished in a number of ways. The applicator can be inserted directly into the tumor volume or adjacent to the tumor volume. Alternatively, an acoustically transparent catheter can be inserted first, either within or adjacent to the tumor. The heating applicator can then be inserted down the catheter to perform the heating. This method of insertion allows for the insertion of other devices and/or agents into the target volume for further diagnosis and treatment, such as miniature RF coils for high resolution MR imaging or spectroscopy of the treatment volume, chemotherapeutic drugs for high dose delivery to the tumor, or gene therapy vectors designed to treat the tumor.

The applicator of the present invention can be used to evaluate the local blood perfusion or thermal diffusivity of the tissue in regions immediately surrounding the applicator. An acoustic pulse with a specific output power can be applied, and the temperature distribution and subsequent decay can be measured with MR thermometry. This allows for an estimation of the effects of blood perfusion based on the decay of the temperature distribution.

Other Applications

The applicator of the present invention can be used to deliver accurately controlled, high intensity ultrasound fields for therapy delivery mechanisms. It has been shown that ultrasound can disrupt the local blood brain barrier (Vykhodtseva et al., 1995; Patrick et al., 1990) and "sonoporate" cell membranes (Miller et al., 1999; Bao et al., 1997) which are known barriers to some forms of drug therapy. An embodiment of the present invention could, thus, be used for various local manipulations of tissue microstructures to enhance delivery, or concentrations of therapeutic agents. Ultrasound-induced temperature elevations can also activate certain enzymes (Vekris et al., 2000) and can potentially enhance delivery mechanisms for some forms of gene therapy (Miller 2000; Lawrie et al. 1999; Kim et al., 1996). Thus, in conjunction with further biological developments, the ability to deliver accurate patterns of high intensity ultrasound could be important for targeting new therapeutic regimes.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Chen L, ter Haar G R, Hill C R 1997 Influence of ablated tissue on the formation of high intensity focused ultrasound lesions *Ultrasound Med Biol* 23(6) 921–931.

Chopra R, Bronskill M J, Foster F S 2000 Feasibility of linear arrays for interstitial ultrasound thermal therapy *Med Phys* (in print).

Chung A H, Hynynen K, Colucci V, Oshio K, Cline H E, Jolesz F A 1996 Optimization of spoiled gradient-echo phase imaging for in vivo localization of a focused ultrasound beam *Magn Reson Med* 36 745–752.

Damianou C, Hynynen K 1993 Focal spacing and near-field heating during pulsed high temperature ultrasound hyperthermia treatment *Ultrasound Med Biol* 19 777–787.

Damianou C A, Sanghvi N T, Fry F J, Maass-Moreno R 1997 Dependence of ultrasonic attenuation and absorption in dog soft tissues on temperature and thermal dose *J Acoust Soc Amer* 102 628–634.

De Poorter J E, De Wagter C, De Deene Y, Thomsen C, Stahlberg F, Achten E 1996 Noninvasive MRI thermometry with the proton resonance frequency (PRF) method: in vivo results in human muscle *Magn Res Med* 33 74–81.

Deardorff D L, Diederich C J, Nau W H 1998 Air-cooling of direct-coupled ultrasound applicators for interstitial hyperthermia and thermal coagulation *Med Phys* 25(12) 2400–2409.

Ebbini E, Cain C 1988 Multiple-focus phased array pattern synthesis: optimal driving-signal distributions for hyperthermia cancer therapy *IEEE Trans Ultrason Ferroelect Freq Contr* 35(5) 561–572.

Fan X, Hynynen K. 1996 Ultrasound surgery using multiple sonications-treatment time considerations *Ultrasound Med Biol* 22(4) 471–482.

Fjield T, Sorrentino V, Cline H, Hynynen K 1997 Design and experimental verification of thin acoustic lenses for the coagulation of large tissue volumes *Phys Med Biol* 42 2341–2354.

Hynynen K, Roemer R. Moros E, Johnson C, Anhalt D 1986 The effect of scanning speed on temperature and equivalent thermal exposure distributions during ultrasound hyperthermia in vivo *IEEE Trans Micro Theory Tech* MTT-34(5) 552–559.

Hynynen K, Freund W, Cline H E, Chung A, Watkins R, Vetro J, Jolesz F A 1996 A clinical noninvasive MRI monitored ultrasound surgery method *RadioGraphics* 16 185–195.

Lafon C, Chapelon J Y, Prat F, Gorry F, Margonari J, Theillere Y, Cathignol D 1998 Design and preliminary results of an ultrasound applicator for interstitial thermal coagulation *Ultrasound Med Biol* 24 113–122.

Lizzi F L, Astor M, Deng C, Rosado A, Coleman D J, Silverman R 1996 Asymmetric focussed arrays for ultrasonic tumor therapy *Proceedings IEEE Ultrasonics Symposium* 2 1281–1284.

Malcolm A L, ter Haar G R 1996 Ablation of tissue volumes using high intensity focused ultrasound *Ultrasound Med Biol* 22(5) 659–669.

McDannold N J, Hynynen K., Wolf D, Wolf G, Jolesz F 1998 MRI evaluation of thermal ablation of tumors with focused ultrasound *J Magn Reson Imaging* 8(1) 91–100.

McGough R J, Wang H, Ebbini E S, Cain C A 1994 Mode scanning: heating pattern synthesis with ultrasound phased arrays *Int J Hyperthermia* 10(3) 433–442.

Moros E G, Roemer R B, Hynynen K 1988 Simulations of scanned focused ultrasound hyperthermia: The effect of scanning speed and pattern on the temperature fluctuations at the focal depth *IEEE Trans Ultrasound Ferroelect Freq Contr* 35(5) 552–559.

Rivens I H, Clarke R L, ter Haar G R 1996 Design of focused ultrasound surgery transducers *IEEE Trans Ultrason Ferroelect Freq Contr* 43(6) 1023–1031.

Thomsen S, 1991 Pathologic analys of photothermal and photomechanical effects of laser-tissue interactions. Photochem. Photobiol. 53, 825–835.

Zimmer J E, Hynynen K, He D S, Marcus F 1995 The feasibility of using ultrasound for cardiac ablation *IEEE Trans Biomed Eng* 42 891–897.

Vykhodtseva N I, Hynynen K, Damianou C 1995 Histologic effects of high intensity pulsed ultrasound exposure with subharmonic emission in rabbit brain in vivo Ultrasound Med. Biol 21(7) 969–979.

Patrick J T, Nolting M N, Goss S A, Dines K A, Clendenon J L, Rea M A, Heimburger R F 1990 Ultrasound and the blood-brain barrier Adv Exp Med Biol 267 369–381.

Miller D L, Bao S, Morris J E 1999 Sonoporation of cultured cells in the rotating tube exposure system Ultrasound Med. Biol 25(1) 143–149.

Bao S, Thrall B D, Miller D L 1997 Transfection of a reporter plasmid into cultured cells by sonoporation in vitro Ultrasound Med. Biol 23(6) 953–959.

Vekris A, Maurange C, Moonen C, Mazurier F, De Verneuil H, Canioni P, Voisin P 2000 Control of transgene expression using local hyperthermia in combination with a heat-sensitive promoter J. Gene Med 2(2) 89–96.

Lawrie A, Brisken A F, Francis S E, Tayler D I, Chamberlain J, Crossman D C, Cumberland D C, Newman C M 1999 Ultrasound enhances reporter gene expression after transfection of vascular cells in vitro Circulation 99(20) 2617–2620.

Miller M W 2000 Gene transfection and drug delivery Ultrasound Med. Biol 26 S59–S62.

Kim H J, Greenleaf J F, Kinnick R R, Bronk J T, Bolander M E 1996 Ultrasound-mediated transfection of mammalian cells Hum Gene Ther 7(11) 1339–1346.

We claim:

1. A device for thermal coagulation of tissue comprising:
   (a) a multifrequency ultrasound transducer for providing acoustic energy at multiple discrete frequencies, said transducer having at least one matching layer comprising a high acoustic impedance material relative to soft tissue and having an acoustic impedance comparable to the acoustic impedance of the transducer for generating acoustic energy at discrete frequencies with high efficiency of acoustic energy transmission;
   (b) a housing for said transducer;
   (c) means for delivery of variable frequency and power to said transducer; and,
   (d) an acoustic window.

2. A device according to claim 1 further comprising a motor control system and means to control frequency and power of ultrasound simultaneously and independently, wherein said motor control system provides rotational control of the device to isolate heating to parts of tissue, the means to control frequency and power allow for adjustment of the depth of thermal coagulation.

3. A device according to claim 2 wherein the transducer is a single element transducer with multiple matching layers.

4. A device according to claim 2 wherein the transducer is a multi-element transducer with individual elements between about 6–20 wavelengths in length, each of which comprises said at least one matching layer.

5. A device according to claim 2 wherein the transducer is a phased array transducer, with elements less than about 1 wavelength in length.

6. A device according to claim 2 wherein at least three transducers are incorporated into the device wherein at least one of each of which comprises:
   (a) a single element transducer with multiple matching layers;
   (b) a multi-element transducer with individual elements between about 6–20 wavelengths in length; or
   (c) a phased array transducer with less than about 1 wavelength in length.

7. A device according to claim 1 wherein the at least one matching layer comprises a ¼ wavelength front matching layer of a high acoustic impedance material, capable of delivery of acoustic energy at two discrete frequencies.

8. A device according to claim 1 wherein the at least one matching layer comprises a ½ wavelength front matching layer of high acoustic impedance material, capable of delivery of acoustic energy at three discrete frequencies.

9. A device according to claim 8 wherein the material is PZT.

10. A device according to claim 9 which is constructed of MR-compatible materials chosen from a metal, ceramic or a polymer.

11. A device according to claim 10 wherein the material is a metal and is brass, copper, or stainless steel.

12. A device according to claim 11 wherein the material is a polymer which is Poly(ether ether ketone)PEEK.

13. A device as claimed in claim 2 wherein said housing comprises tube means for infusing a therapeutic agent into a patient.

14. A device of claim 2 further comprising an acoustically transparent catheter.

15. A device according to claim 1, wherein the high acoustic impedance material has an acoustic impedance similar to that of the transducer.

16. A device according to claim 1, wherein the multiple discrete frequencies are separated by a factor of at least two.

17. A device according to claim 1, wherein the at least one matching layer comprises a ¼ wavelength matching layer of a high acoustic impedance material and a ¼ wavelength intermediate acoustic impedance matching layer, capable of delivery of acoustic energy at three discrete frequencies.

18. A device according to claim 1, wherein the at least one matching layer comprises a ½ wavelength matching layer of a high acoustic impedance material and a ¼ wavelength intermediate acoustic impedance matching layer, capable of delivery of acoustic energy at four discrete frequencies.

19. A method for interstitial ultrasound thermal therapy of tissue comprising:

(a) determining target tissue volume from images;

(b) planning a route of insertion for a device and a heating regime based on the images, the heating regime comprising a sequence of scan rates, transmission frequencies and powers as a function of device angle;

(c) inserting the device into a desired location for the interstitial thermal coagulation of said target tissue volume, said device comprising a multifrequency ultrasound transducer for providing acoustic energy at multiple discrete frequencies at high efficiency, said transducer having at least one matching layer comprising a high acoustic impedance material relative to soft tissue and having an acoustic impedance comparable to the acoustic impedance of the transducer;

(d) implementing the heating regime by delivering the acoustic energy to the target tissue volume from the device, the acoustic energy having various frequencies selected from the multiple discrete frequencies, and by rotating and translating the device for producing a thermal lesion conformal to said target tissue volume; and (e) assessing the thermal lesion with imaging.

20. A method according to claim 19 wherein the transducer of the device is a single element transducer with multiple matching layers.

21. A method according to claim 20 wherein the at least one matching layer comprises a ¼ wavelength front matching layer of a high acoustic impedance material, capable of delivery of acoustic energy at two discrete frequencies.

22. A method according to claim 21 wherein the material of the transducer is PZT.

23. A method according to claim 22 wherein the device is constructed of MR-compatible materials chosen from a metal, ceramic or a polymer.

24. A method according to claim 23 wherein the material of the device is a metal and is brass, copper, or stainless steel.

25. A method according to claim 23 wherein the material is a polymer which is Poly(ether ether ketone)PEEK.

26. A method according to claim 20 wherein the at least one matching layer comprises a ½ wavelength front matching layer of high acoustic impedance material, capable of delivery of acoustic energy at three discrete frequencies.

27. A method according to claim 19 wherein the transducer of the device is a multi-element transducer with individual elements between about 6–20 wavelengths in length, each of which comprises said at least one matching layer.

28. A method according to claim 19 wherein the transducer of the device is a phased array transducer, with elements less than about 1 wavelength in length.

29. A method according to claim 19, wherein at least three transducers are incorporated into the device wherein at least one of each of which comprises:

(a) a single element transducer with multiple matching layers;

(b) a multi-element transducer with individual elements between about 6–20 wavelengths in length; or (c) a phased array transducer with less than about 1 wavelength in length.

30. A method as claimed in claim 19 wherein the housing of the device comprises tube means for infusing a therapeutic agent into a patient.

31. A method of claim 19 where the device further comprises an acoustically transparent catheter.

32. A method according to claim 19, wherein step (d) further comprises varying power of the acoustic energy for adjusting depth of penetration of the acoustic energy.

33. A method according to claim 19, wherein step (d) further comprises varying the frequency by at least a factor of two.

* * * * *